United States Patent [19]

Norman et al.

[11] Patent Number: 5,008,907
[45] Date of Patent: Apr. 16, 1991

[54] THERAPY X-RAY SCANNER

[75] Inventors: Amos Norman, Woodland Hills; Keisuke S. Iwamoto, Monterey Park, both of Calif.

[73] Assignee: The Regents of the University of California, Oakland, Calif.

[21] Appl. No.: 359,159

[22] Filed: May 31, 1989

[51] Int. Cl.⁵ .............................. A61N 5/10
[52] U.S. Cl. ........................... 378/65; 378/4; 378/8; 378/9; 378/17
[58] Field of Search ............ 378/65, 9, 17, 8, 4

[56] References Cited

U.S. PATENT DOCUMENTS

| | | | |
|---|---|---|---|
| 4,112,303 | 9/1978 | Brandt | 378/17 |
| 4,384,359 | 5/1983 | Franke | 378/9 |
| 4,689,670 | 8/1987 | Okazaki | 378/8 |
| 4,868,843 | 9/1989 | Nunan | 378/65 |

OTHER PUBLICATIONS

"A New Superficial X-Ray Therapy Unit", Lillicrap et al, British Journal of Radiology, vol. 47, pp. 193–195, 3/1974.

Iwamoto et al., "Radiation dose enhancement therapy with iodine in rabbit VX-2 brain tumors", *Radiotherapy and Oncology* 8:161–170 (1987).

Primary Examiner—Craig E. Church
Attorney, Agent, or Firm—Charles Berman

[57] ABSTRACT

A CT therapy scanner moves a therapy x-ray source in an arc about a subject. A tumor or lesion is isocentered by the x-ray beam which is a pencil beam. A fan beam, from which the pencil beam is obtained, provides for visualization thereby to ensure that x-ray therapy is accurately delivered. A collimator provides for the conversion of a fan beam to a pencil-fan beam characteristic.

40 Claims, 4 Drawing Sheets

FIG. 3B

THERAPY X-RAY SCANNER

BACKGROUND

This invention relates to x-ray beam therapy. In particular, it relates to computer tomographic scanner and their use in delivering a therapy dose of x-rays.

A computer tomography ("CT") scanner can localize precisely many tumors and other lesions in the brain. After the CT scan is obtained, a patient is taken to another location for treatment with high energy photons from a gamma knife or a linear accelerator.

The proper alignment of the patient in the radiation field requires that the lesion in the brain must be located with respect to external markers provided by a stereotactic frame. This is attached to the skull by surgical screws. Mounting the frame, locating the lesion with respect to the coordinates and then directing the therapy beam is a difficult and time consuming task.

Current stereostatic therapy procedures are time consuming an unpleasant for the patient. The stereostatic locating operation alone is relatively traumatic since holes are drilled into the skull while the patient receives only a local anesthetic.

Once the device is absolutely secure on the patient's head, the patient is transported to a diagnostic x-ray room in order to localize the brain tumor with respect to setting the coordinates on the stereostatic device. Finally the patient is transported to a third room for the actual radiation treatments by the gamma knife (an array of cobalt-60 sources focused at a point) or other high energy photon source such as the linear accelerator.

The knife is stable but expensive and inflexible in the volume irradiated. Linear accelerators tend to wobble during rotation, limiting precision, and are limited to a single arc of rotation. Moreover, the large exit doses of high energy photon beams place at risk relatively large volumes of normal tissue.

CT scanners are well known for use as diagnostic tools. For this purpose, the CT scanner uses an x-ray source mounted on a gantry which can rotate in an arc about a subject located on a couch at about the axis of rotation. A gantry can be tilted about the axis of rotation such that different slices of image can be obtained of the subject. CT scanners have developed for different diagnostic purposes, but in the Applicant's knowledge, have not been used for therapy purposes.

Different scanning mechanisms have been employed in CT scanners. Commonly, the first generation scanner used a pencil beam which moved linearly across the entire head of the subject in a parallel fashion to generate a first series of data at a scan 45° position. Thereafter, the x-ray tube was moved to the scan 90° position, 45° away and the same pencil beam was then directed linearly across the entire head. This was repeated at the scan 135°.

In a second generation CT scanner, the beam was replaced with a narrow fan beam but essentially the linear direction of the beam across the entire patient's head was effected in each of three scan positions.

In the third generation CT scanner, a wide fan beam was used sufficient to encompass the entire width of the patient. The gantry moved in a rotating action continuously. The fourth generation scanner permits the tube to rotate through an arc of 360° with a wide fan beam encompassing the entire width of the patient's head.

Although a fan beam is useful for obtaining a high volume of data for multiple detectors quickly, it is not appropriate for use in therapy applications. Additionally, the x-ray tube is in the orthovoltage range at about 120 KVP to about 300 KVP. Such a voltage range is conventionally suitable only for diagnostic purposes.

When x-ray therapy is effected, it is currently regarded as desirable to use a voltage range in the order of 2 to 6 MEV since this can deliver a high voltage dose to a targeted tumor. In addition, the skin dosage from such a beam is relatively lower than that from a orthovoltage beam. High KVP x-ray systems are poor for visualization since there is too little contrast with the different tissue. The low KVP beam, on the contrary, is effective for diagnostic purposes since there is good contrast. The voltage, however, is unsuitable for effective treatment of deep tumors with the conventional 2 or 3 fixed fields.

There is accordingly a need to provide an improved system for therapy which avoids the complex mechanical systems currently in use and which can use the benefits of diagnostic CT scanners.

SUMMARY

By this invention a CT scanner is used as a therapy x-ray machine. In this way, a patient is scanned and treated on the same table as for diagnostics. The isocenter of the therapy beam is placed precisely in the center of the lesion and the beam is readily restricted to just those planes of the lesion. The position of the lesion in the x-ray beam is monitored continuously during therapy.

According to the invention, apparatus for delivering a therapy dose of x-rays to a subject comprises moving an x-ray source in an arc about the subject. An x-ray beam from the source is isocentered on a selected target on the subject. The beam directed to the isocenter in the subject is a pencil beam.

A collimator converts the fan beam of the CT scanner to a small round or rectangular pencil beam required during the arc therapy mode. This is accomplished with an orthovoltage x-ray beam. The fan beam in part penetrates the collimator such as to permit visualization of the tumor while the pencil beam penetrates the aperture through the collimator to permit therapy dosages of x-ray to be delivered to the lesion. This enables visualization while effecting therapy.

By using an orthovoltage source and rotating the beam about the subject, different portions of the skin is subjected to the x-ray beam which is directed to the isocenter. This retains the overall skin dosage on anyone location relatively low. Similarly, the low exist dose of an orthovoltage beam ensures that relatively high dosages are directed to the lesion at the isocenter. Low dosages only are directed to other parts of the subject.

The position and cross-section of the therapy beam is imaged by the scanner during therapy. Multiple arc therapy can easily be done by tilting the gantry of the CT scanner on which the x-ray tube is mounted.

The apparatus can also be for use as a conventional diagnostic unit. Accordingly, the scanner diagnostic tube can be replaced with a therapy tube, which will also be used for diagnostics.

DRAWINGS

Figure 4:
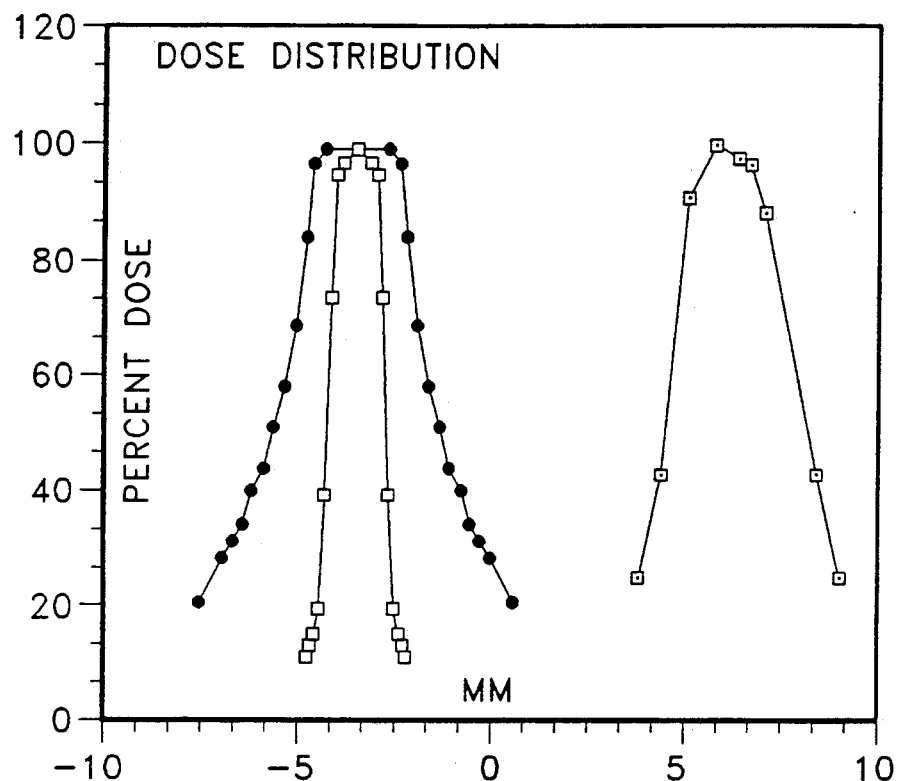

FIG. 4 depicts the dose distributions measured in planes parallel and perpendicular to the table through the isocenter. These 150° arcs were used with a field size of 1 cm×2 cm. The CT scanner was operated at 120 KVP, and the isocenter was 7.5 cm below the surface of the head.

Figure 5:
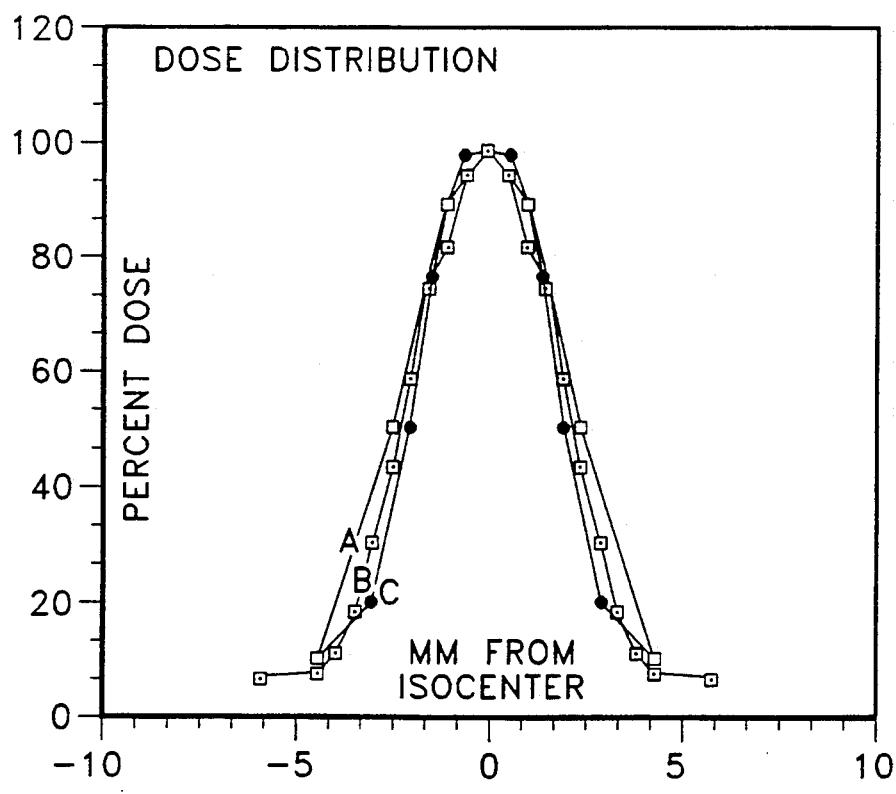

FIG. 5 depicts a comparison of the dose distributions from the CT scanner with those from two gamma knives. The CT scanner operated at 140 KVP with a field size of 3 mm×3 mm gave distribution B in the plane of the table when the isocenter was 7.5 cm below the surface of the head. Nine arcs were used. The distributions marked A and C are for the two gamma knife systems.

Figure 6A:
Figure 6B:
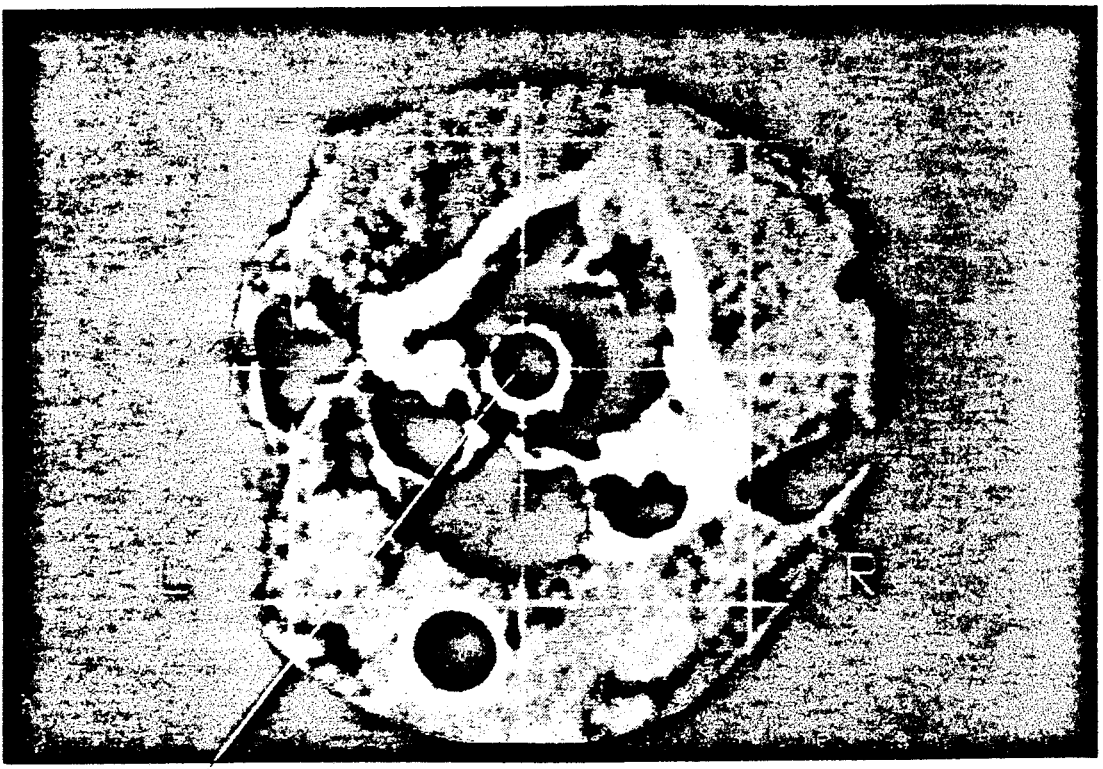

FIGS. 6A and 6B are photograph scans through a brain tumor in CT diagnostic configuration, A, and in therapy configuration, B.

DESCRIPTION

Figure 1:
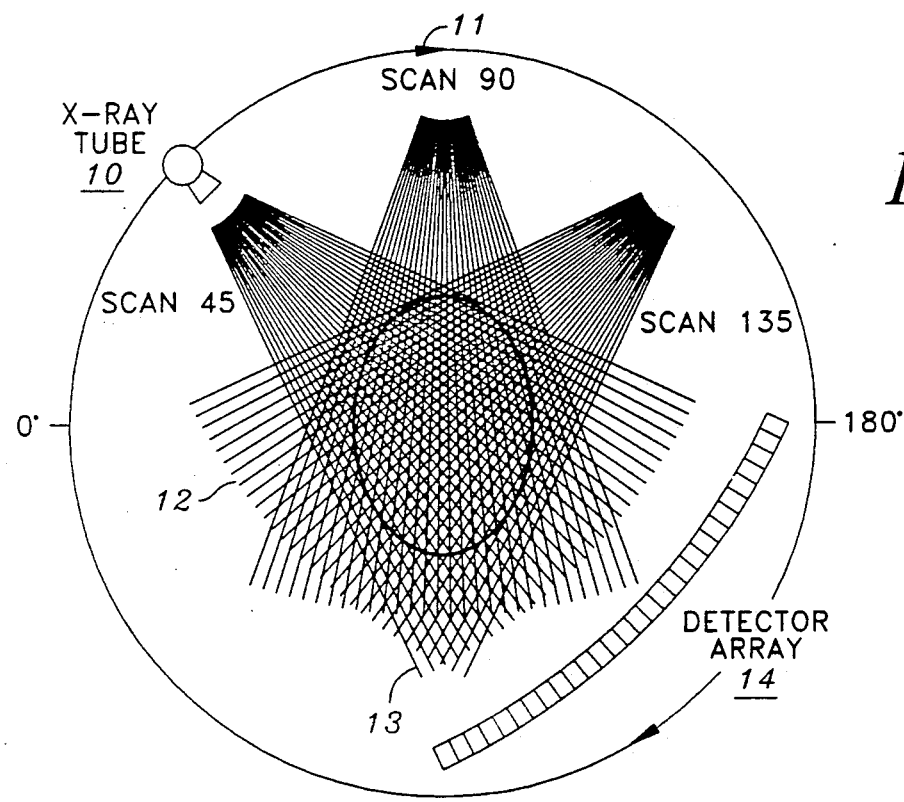
FIG. 1 is a prior art depiction of a CT scanner with a wide fan beam moving over the entire subject.

In FIG. 1 a third generation CT scan used for diagnostic is illustrated. The x-ray tube 10 tracks a path as indicated by arrow 11 around a head 12. A wide fan beam 13 from the x-ray tube 10 is directed over the entire head 12. A detector ray 14 is arranged oppositely to the x-ray tube 10. At all times during the scanning of the head 12 by the x-ray tube 10, beams 13 completely subject the head to x-rays.

Figure 2:
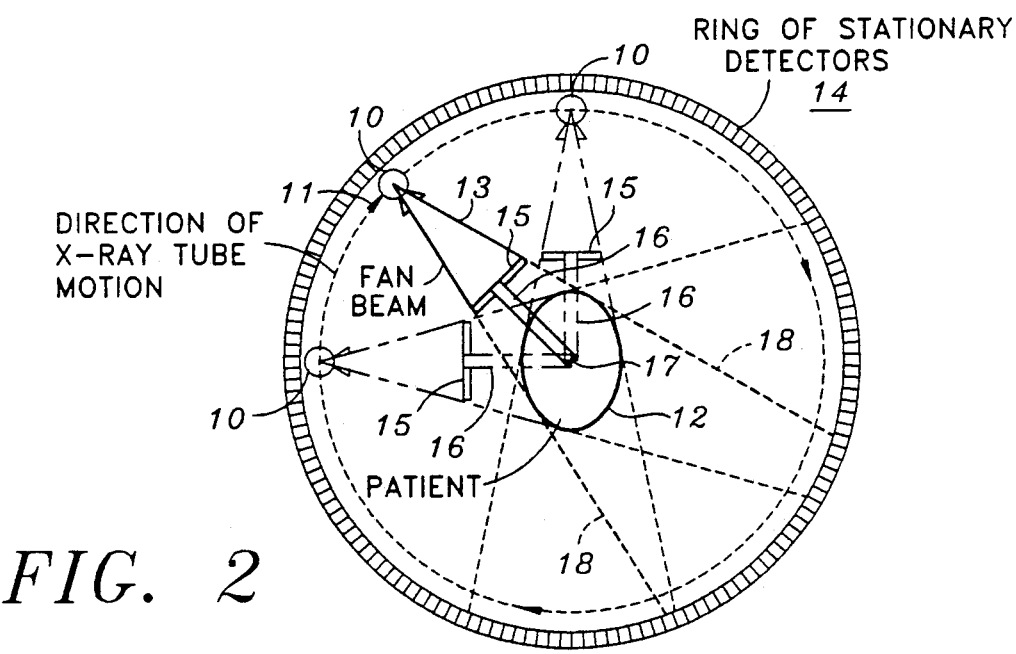
FIG. 2 is a depiction of a CT scanner arranged for a therapy mode.

In FIG. 2 there is illustrated the CT scan of a fourth generation where the x-ray tube 10 can rotate through 360° as indicated by arrow 11. A ring of stationary deflectors 14 is located outside of the tube perimeter. The x-ray tube 10 emits a fan beam 13 which through collimator 15 is reduced to a pencil beam 16 which is focused at the isocenter 17 in the head of the patient. In the example in the FIG. 2, this is in the center of the head of the patient 12. During this time, the fan beam 13 is attenuated as indicated by the phantom line 18 and is still directed over the head of the patient. This is used for viewing the head of the patient in the manner which will be described. In other examples, the isocenter 17 may be in a different location in the head 12.

Figure 3A:
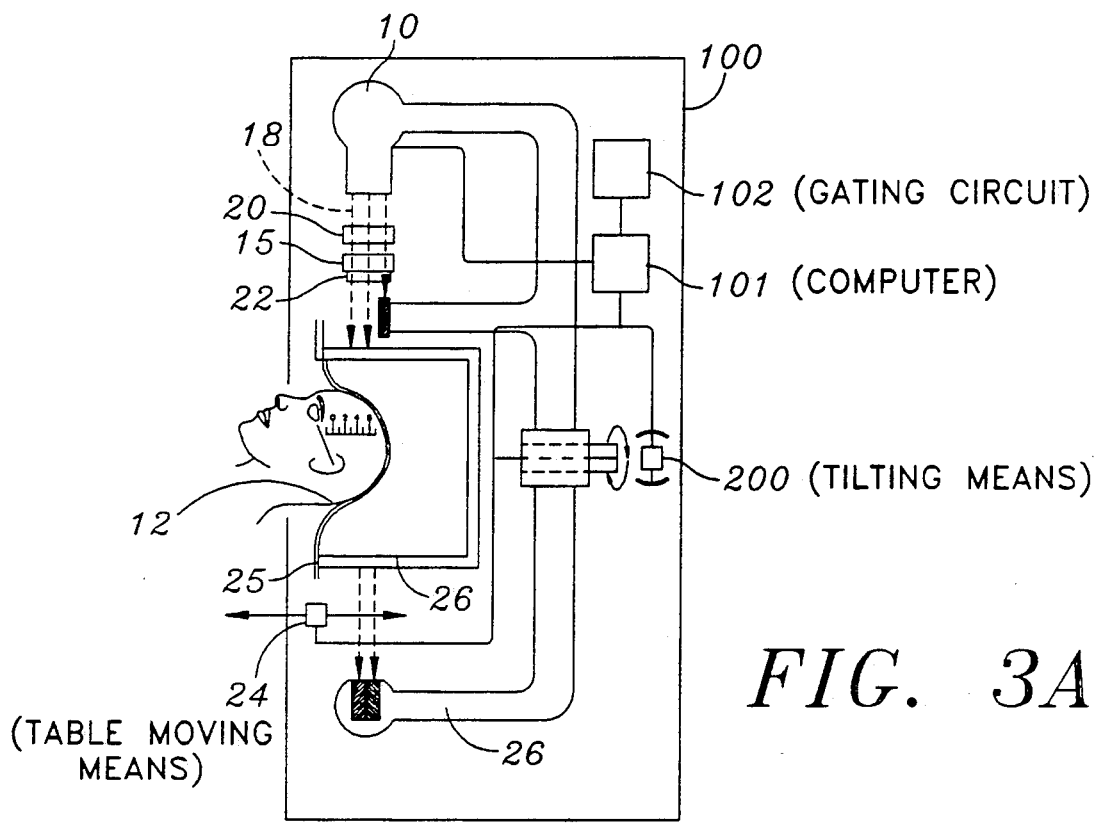
FIG. 3A illustrates diagrammatically a CT scanner with its gantry.
Figure 3B:
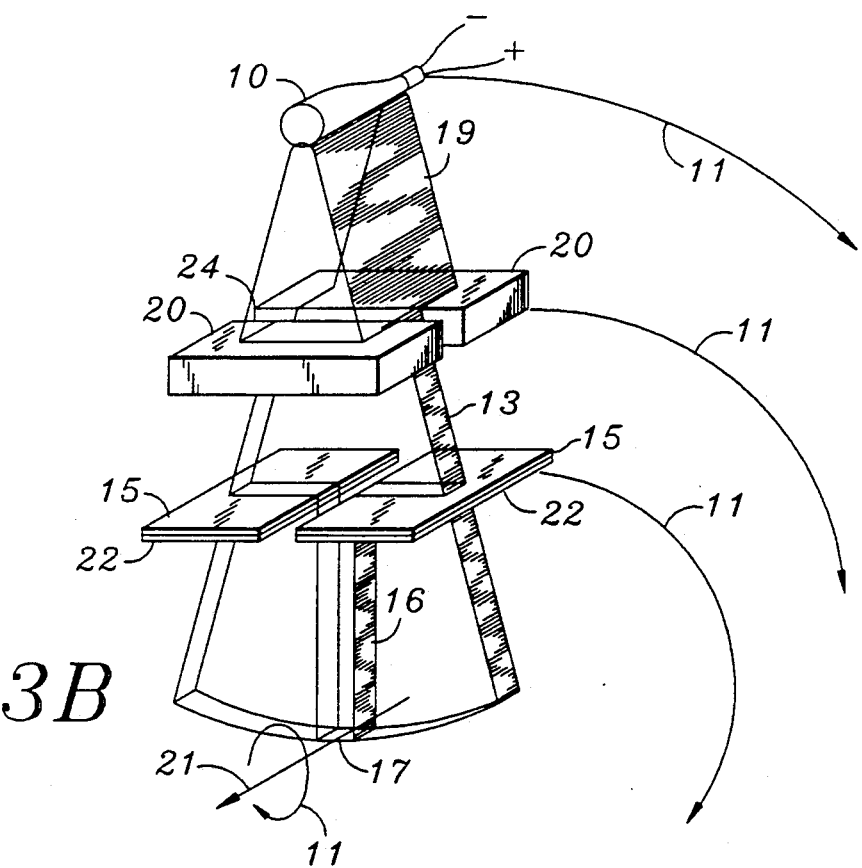
FIG. 3B is a perspective diagrammatic view of an x-ray tube generated fan beam and collimator for reducing the fan beam to a pencil beam.

In FIG. 3B, a collimator system 15 is indicated in greater detail. The fan beam 13 which interacts with collimator 15 emanates from the x-ray source or tube 10 as a broad beam 19. A first pair of collimator shutters 20 in the CT scanner limits the width of the beam to form the fan beam 13. The collimator sheets or plates 15 then reduce the width of the fan beam 13 to the pencil beam shape 16. The pencil beam is directed to the isocenter 17 which is at the axis of rotation, namely, the location of a tumor or lesion.

Should the tumor be located in a position differently to the isocenter of the machine 17 then a couch on which the patient is located is moved up or down or the patient is moved left or right so that the isocenter 17 is always at the center of rotation. The arrows 11 in FIG. 3B indicate the components which rotate about the isocenter 17. The axis of rotation is indicated by line 21. Second collimator shuttered 22 are illustrated in parallel location below the collimator shutters 15. With the collimator shutter 22 removed from the aperture, a stronger diagnostic picture can be obtained on the detectors remotely located relative to the isocenter. With the collimator sheets 22 in position about the aperture a greater thickness is presented to the fan beam 13 and the diagnostic viewing is reduced. It is still sufficiently strong to locate the view of the head and the lesion. The pencil beam 16 is directed to the lesion. In this manner, an adjustable collimator is provided.

The collimator 15 and 22 added to the CT scanner blocks radiation to many of the detectors 14. The CT scanner is able nevertheless to reconstruct images of the illuminated portion of the head 12 and to show clearly many details in the head. It is feasible, therefore, to monitor the position of beam 16 during therapy without the removal of the collimating lead strips 15 and 22. Moreover, the cross-section 23 (FIG. 6B) of the therapy beam 16 is also shown which is helpful in treatment planning and in confirming the proper placement of the tumor in the beam 16.

The adjustable collimators 15 and 22 permit quick changes from an imaging or diagnostic mode to a therapy mode. Adjustments to permit optimal field sizes for each arc is obtained. A machine can also provide cooling to the x-ray tubes 10 so that they can be operated continuously and be operable at higher orthovoltages. In this manner, large radiation dose required for radiosurgery can be obtained quickly.

To take advantage of dose enhancement in brain tumors, when the tumor is loaded with iodine. Better imaging can be obtained with iodine contrast media. Also, it is best to operate the x-ray tube at 120 or 140 KVP rather than at a higher KVP. A high dose rate can then be achieved by mounting several x-ray tubes 10 on the gantry pointing to the isocenter 17. For treatments not involving iodine dose enhancement a higher KVP may be preferable since it gives a higher dose rate and less bone absorption.

Ideally, the CT therapy apparatus will permit a variety of options concerning KVP and collimator settings. It is feasible to convert existing CT scanners to a CT therapy scanner for use for treating tumors in the brain and elsewhere in the body. A significant important advantage is that the treated volume can be visualized directly at any time during the course of therapy without moving the patient.

EXAMPLES

Experiments were carried out on a GE 9800 CT scanner. The collimator 20 forms a long slit 24 which can be adjusted to give a slice thickness from 1 mm to 1 cm. To produce rectangular or square fields in sizes suitable for therapy lead strips 15 were taped across the slit 23. Two field sizes were explored: 1 cm×2 cm and 3 mm×3 mm.

To explore the dose distribution from this CT therapy scanner the head of a Rando phantom was placed on a table 36. The phantom is sliced in planes parallel to the table 36. X-ray film was placed between sections of the phantom. After exposure the distribution of optical density was measured with a densitometer and the radiation dose was determined from a calibration curve.

In order to explore the field in planes close to the plane containing the isocenter the table 36 was moved up or down in 1 mm steps and the dose distribution was measured. The isocenter was placed 7.5 cm below the top of the head 12 so that the full effect of scattering deep within the brain would be observed. For the 1 cm×2 cm field three arcs were used. In one arc, the plane of rotation was perpendicular to the table, and in the other two arc, the planes were displaced by +1−20° from the vertical. For the 3 mm×3 mm field 9 arcs were used, these were at 0,±/−5,10,15, and 20° from the vertical. The arcs were limited to 150° by wrapping a lead sheet around the phantom. For the large field the scanner was run at 120 KVP, for the small field at 140 KVP. CT scans of the Rando phantom at these settings gave CT numbers for the bone and soft tissues consistent with an effective energy for the x-ray beam of 60 and 70 KEV respectively.

To calculate dose distributions in the brain from the CTX x-ray beam a water tank was irradiated with a horizontal x-ray beam from a therapy machine operated at 120 KVP. The top of a human skull was suspended in the tank 1 cm from where the beam entered the tank. The dose rate was explored to the left and right of the skull bone with an ionization chamber. The depth doses for seven field sizes were determined and entered into the AECL Theraplan and the dose distribution was calculated for a lesion 5 cm below the surface of the head using a single 180° arc.

A similar calculation was made for a 250 KVP x-ray beam and a cobalt-60 therapy machine. The transmission of the cobalt gamma rays and the 250 KVP x-rays through the bone were underestimated by using a density of 1 for the bone. The correct transmission was used for the 120 KVP beam, however its absorption by the bone was underestimated by about a factor of 2 by ignoring the photoelectric component. These approximations do not greatly affect the calculated dose distributions in the brain.

FIG. 4 shows the measured dose distributions in three directions when three arcs are used about an isocenter 7.5 cm below the surface of the head 12. Two of the directions are in a plane through the isocenter parallel to the table top, the other is in a plane through the isocenter perpendicular to the table top. The distribution is symmetrical in the first plane, but asymmetric in the second. As the number of arcs increases this asymmetry becomes less pronounced. Since the collimator 20 opens only to 1 cm in one direction, treating fields larger than 1 cm in the perpendicular direction requires that the treatment couch be moved. The larger the field size the fewer planes can be treated without overlap of the dose distributions. For radiation doses of 15 to 25 Gy in 1 fraction it is undesirable to use field sizes much above 1 cm×1 cm.

FIG. 5 compares the dose distribution B using nine arcs with the CT scanner therapy scanner with the dose distributions from two gamma knife systems A and C. The three distributions are very similar. Even at the deepest portion of the brain, some 7.5 cm below the surface of the head, the CT therapy scanner appears to compare favorably with distributions obtained with the gamma knife.

FIG. 6A shows a CT scan through a brain tumor in a dog. The scan provides information not only about the position of the tumor within the skull but also its distance from the isocenter 17 so that moving the tumor to the isocenter 17 is relatively simple. In FIG. 6B the tumor has been moved to the isocenter 17, the collimator 15 has been modified to approximately a 1 cm×1 cm square and therapy has been started with one complete circle. The image of the cross-section 23 of the therapy beam 16 can be seen at the position of the tumor together with a surprising amount of detail within the skull.

The dose delivered to the center of the head 17 from a complete rotation of the CT therapy scan operated at 140 KVP is about 3 rads. A rotation takes about 2 seconds. Thus if the x-ray tube 10 could be operated continuously, the dose rate at the center will be about 90 rads min. The relative biological effectiveness of the x-ray beam 16 versus the cobalt 60 gamma rays is 1.6 to 1.8. Thus the dose rate is equivalent to about 120 rads min of the gamma rays. The dose rate will be higher for lesions closer to the surface of the head. However, the effective dose rate will be much lower, since it will be necessary to allow the diagnostic x-ray tube to cool periodically. The degree lower will depend on the heat capacity of the specific x-ray tube. With a graphite tube it is possible to obtain 300 scans per hour which implies as much as 9 Gy per hour at the center of the head. The biological effect is approximately equal to that from a 15 Gy radiation dose from the gamma knife or a linear accelerator.

Adding collimator 15 and selectively collimator 22 to the scanner 100 provides for adjustment and variation of the beam 16 directed to the head 12. For positioning and viewing in diagnostics, the shutter or shields 22 are removed from the aperture or slit 24. During therapy, the shields 22 are preferably located in position parallel with the sheets 15. This provides for continuous monitoring of the patient during treatment. Reconstruction of the beam 16 or 18 cross-section aids the therapy planning and permits for rapid repositioning before each dose fraction. Transmission through the collimator can be about 1% and through the aperture the pencil beam transmission is about 100%. The collimator 15 thickness is about 5 millimeters and the aperture is defined as a 5 millimeter to 10 millimeter rectangular aperture.

Since an orthovoltage x-ray tube 10 in a range of 120 KVP and 250 KVP is used, shielding of other parts of the body can be effected with thin layered lead sheets. This is in contrast to using the MEV range of x-ray tube normally used for therapy. By having the orthovoltage scan traverse about the head the skin dosage at any particular point is minimized. Exit dosage is further minimized by loading the tumor with iodine. Iodine has both the advantage of being an effective x-ray contrast medium to assist in diagnostics and vision and also an enhancement of the radiation dose in the tumor. This consequently decreases the exit dose. With this system, therefore, highly accurately directed therapy x-ray doses are provided to a tumor or lesion without the disadvantages associated with statatic devices and gamma knives.

As necessary, the field sizes can be controlled with the collimator 15 and 22 and a field sizes can be extended by moving the table by means 201 as diagrammatically indicated 36. The direct control between the x-ray source or tube 10 and the detectors 14 and the computer 101 interface permits for accurate delivery of therapy x-ray dosages. Multiple arcs are obtained by tilting the gantry 26 as required by means 200 as diagrammatically indicated.

By replacing the diagnostic tube normally in a CT scanner 100 with a duty rated therapy-type tube 10 continuous operation of the x-ray tube 10 can be effected as diagrammatically indicated. This increases the average dose rate. By using such a tube 10, oil cooling or cooling by other heat transfer agents is possible and, hence, there will be less expensive costs associated with tube replacement, and higher effective dose rates.

In order to deliver therapy to moving organs of a subject, a gating circuit 102 is provided to the system to permit for accurate imaging and dose delivery. The x-ray tube 10 is gated to operate in accordance with the moving organs so that pulsing x-rays are delivered only as appropriate when an organ is at an isocenter as required. Providing two or more tubes 10 on the gantry 26, with common isocenter, can also increase the dosage rate.

By having the collimator 15 constructed to allow some leakage, the diagnostic vision or image is improved so that the system can provide for both dual diagnostics and therapy functions. Note that even without leakage some imaging is provided probably as the result of scattering. This permits, for example, visualization of lead markers on the patient during therapy.

The CT therapy scanner saves time, space and money, and greatly lessens discomfort for the patient. Moreover, with the dose enhancing effect of the iodinated contrast medium, it provides a better does distribution than high energy photons around the treated volume. No operation is required on the patient and the entire procedure takes place in one room. The patient merely lies on the table and the CT therapy scanner first localizes the tumor using its CT scanner capabilities. The table is then positioned such that the tumor is at the center of rotation of the therapy x-ray beam. Finally the CT therapy scanner proceeds with its dynamic three-dimensional arc therapy. The dynamic three-dimensional arc therapy consists of the rotation of a thin x-ray beam in an arc in several different planes, made possible by tiling the rotating gantry of the CT therapy scanner by plus or minus 25 degree from the vertical and by moving the table. There is overlap only at the tumor volume.

Many other examples of the invention exist, each differing from the other in matters of detail only. The scope of the invention is defined solely by the appended claims.

We claim:

1. Apparatus for delivering a therapy dose of x-rays to a subject comprising means to move an orthovoltage range x-ray source mounted on a computed tomographic scanning unit including a source, detector, and data processing means for displaying a cross-sectional image of a selected portion of the subject in an arc about the subject such that an x-ray beam from the source is isocentered on a selected target in the subject, and means for directing the beam as a pencil beam to the isocenter in the subject to deliver therapy x-rays.

2. Apparatus as claimed in claim 1 wherein the beam generated by the x-ray source is converted to a fan beam, and including at least one collimator for converting the fan beam to the pencil beam.

3. Apparatus as claimed in claim 1 including an x-ray tube rated according to therapy-type characteristics, such a tube employing selectively oil or other heat transfer agent for cooling.

4. Apparatus as claimed in claim 2 wherein the aperture size defined by the collimator is about a 5 millimeter to 10 millimeter rectangular aperture and there is a size thickness of about 5 millimeters.

5. Apparatus as claimed in claim 2 wherein the collimator is adjustable so as to define the shape and attenuation characteristics in converting the fan beam to a pencil beam.

6. Apparatus as claimed in claim 5 wherein the collimator contains components to have different thickness of shutter.

7. Apparatus as claimed in claim 6 wherein the collimator contains at least two different thicknesses of shutter, such that when one thickness of shutter is closed, a first beam characteristic is developed, and when the second collimator shutter is closed, a second beam characteristics is generated, and when both shutters are closed a different beam characteristics is generated.

8. Apparatus as claimed in claim 6 such that when the first collimator is located in operative position the fan beam is directed to the subject in addition to the pencil beam, the fan beam acting to define the location of the subject relative to the x-ray source, and when the second collimator is located in operative position the fan beam outside the field of the pencil beam is further reduced.

9. A method for delivering a therapy dose of x-rays to a subject comprising moving an orthovoltage range x-ray source mounted on a computed tomographic scanning unit including a source, detector, and data processing means for displaying a cross-sectional image of a selected portion of the subject in an arc about the subject such that an x-ray beam from the source is isocentered on a selected target in the subject, and directing the beam as a pencil beam to the isocenter in the subject to deliver therapy x-rays.

10. A method as claimed in claim 9 including converting a generated x-ray beam into a fan beam and collimating the fan beam to the pencil beam.

11. A method as claimed in claim 10 such that in a first operative position the fan beam is directed to the subject in addition to the pencil beam, the fan beam acting to define the location of the subject relative to the x-ray source, and in a second operative position the fan beam outside the field of the pencil beam is reduced.

12. A method as claimed in claim 11 including operating the x-ray tube continuously thereby to increase the average dose rate directed to the isocenter.

13. A method as claimed in claim 9 including moving the subject over a defined area relative to the x-ray source.

14. A method as claimed in claim 9 including mounting the x-ray source on a gantry, and moving the gantry into different titled directions relative to the subject.

15. A method as claimed in claim 9 including locating several x-ray sources for movement in an arc about the subject.

16. A method as claimed in claim 9 including operating the x-ray tube continuously thereby to increase the average dose rate directed to the isocenter.

17. A method as claimed in claim 9 including operating the x-ray source in response to moving organs in the subject whereby the beam is directed and operational on alignment of the organ in the subject with the isocenter in the subject.

18. A method as claimed in claim 9 including rating an x-ray tube according to therapy-type characteristics, such a tube employing selectively oil or other heat transfer agent for cooling; and including operating the x-ray tube continuously thereby to increase the average dose rate directed to the isocenter.

19. A method as claimed in claim 9 including operating the scanner in diagnostic mode.

20. A method as claimed in claim 9 including loading a target in the subject with an x-ray enhancement medium thereby to increase the x-ray absorption at the isocenter.

21. A method according to claim 9 including increasing the dose rate to the isocenter in the subject and reducing the relative dosage absorption in the skin of the subject and the exit dosage beyond the isocenter.

22. A method for localizing a lesion within a cross-section of a patient and delivering multiple arc radiation therapy with x-rays to the lesion and simultaneously imaging both the cross-section being irradiated and the position of the therapy beam in the irradiated section comprising mounting an x-ray tube on a gantry to be rotatable in a plane about an isocenter, tilting the gantry relative to the vertical, moving the patient relative to the gantry, an array of detectors being located opposite the x-ray tube, shaping a beam from the x-ray tube to produce a fan beam between about 120 to about 250 KVP to encompass a narrow section of the patient and then fall on the array of detectors, processing information from the detectors to produce and display cross-sectional images to localize the lesion, moving the patient until the isocenter is centered at the lesion, producing a beam with a field size and shape to at least partly encompass the lesion, adjusting the beam for arc therapy radiation, directing multiple arcs of therapy radiation about the isocenter, tilting the gantry without repositioning the patient, processing information obtained by the detectors during the arcs of therapy to obtain cross-sectional images displaying details of the anatomy of the patient and a cross-section of the beam at the isocenter.

23. Apparatus for delivering a therapy dose of x-rays to a subject comprising a computed tomography scanner including a source, detector, and data processing means for displaying a cross-sectional image of a selected portion of the subject having means to move an orthovoltage range x-ray source in an arc about the subject such that an x-ray beam from the source is isocentered on a selected target in the subject, and means for directing the beam as a pencil beam to the isocenter in the subject, and including collimator means for converting the x-ray beam to the pencil beam.

24. Apparatus as claimed in claim 23 including means for operating the scanner in diagnostic mode.

25. A method of treating a tumor in the head of a subject by delivering a therapy dose of x-rays to the tumor comprising moving an orthovoltage range x-ray source on a computed tomography scanning unit including a source, detector, and data processing means for displaying a cross-sectional image of a selected portion of the subject in an arc about the subject such that an x-ray beam from the source is ioscentered on the tumor, and directing the beam as a pencil beam to the isocenter in the subject to deliver therapy x-rays.

26. A method as claimed in claim 25 wherein the beam is collimated to a pencil beam.

27. A method as claimed in claim 26 including loading the tumor with iodine thereby to enhance the x-ray absorption at the isocenter.

28. A method according to claim 26 including the step of increasing the dose rate to the isocenter in the subject and reducing the relative dosage absorption in the skin of the subject and the exit dosage beyond the isocenter.

29. Apparatus for delivering a therapy dose of x-rays to a subject comprising means to move an orthovoltage range x-ray source mounted on a computed tomographic scanning unit including a source, detector, and data processing means for displaying a cross-sectional image of a selected portion of the subject in an arc about the subject such that an x-ray beam from the source is isocentered on a selected target in the subject, and means for directing the beam as a pencil beam to the isocenter in the subject, wherein the beam is generated by an x-ray source, and including at least one collimator for converting the beam to the pencil beam, such that the pencil beam delivers a therapy dose of x-rays to the isocenter and wherein the beam simultaneously provides an imaging cross-section about the isocenter.

30. Apparatus as claimed in claim 29 wherein the collimator is adjustable so as to define the shape and attenuation characteristics in converting the beam to a pencil beam.

31. Apparatus as claimed in claim 29 including an x-ray tube rated according to therapy-type characteristics, such a tube employing selectively oil or other heat transfer agent for cooling.

32. A method for delivering a therapy dose of x-rays to a subject comprising moving an orthovoltage x-ray source mounted on a computed tomographic scanning unit including a source, detector, and data processing means for displaying a cross-sectional image of a selected portion of the subject in an arc about the subject such that an x-ray beam from the source is isocentered on a selected target in the subject, and directing the beam as a pencil beam to the isocenter in the subject, including converting a generated x-ray beam into a pencil beam, such that the pencil beam delivers a therapy dose of x-rays to the isocenter and wherein the beam simultaneously provides an imaging cross-section about the isocenter.

33. A method as claimed in claim 32 including operating the x-ray source in response to a moving organ in the subject whereby the beam is directed and operational in alignment of the organ in the subject with the isocenter in the subject.

34. A method as claimed in claim 32 including moving the subject over a defined area relative to the x-ray source.

35. A method as claimed in claim 32 including mounting the x-ray source on a gantry, and moving the gantry into different tilted directions relative to the subject.

36. A method as claimed in claim 32 such that the beam is directed to the subject to define the location of the isocenter and the subject relative to the x-ray beam.

37. A method as claimed in claim 32 including operating the x-ray tube continuously thereby to increase the average dose rate directed to the isocenter.

38. A method as claimed in claim 32 including loading a target in the subject with an x-ray enhancement medium thereby to increase the x-ray absorption at the isocenter.

39. A method according to claim 32 including increasing the dose rate to the isocenter in the subject and reducing the relative dosage absorption in the skin of the subject and the exit dosage beyond the isocenter.

40. A method of subjecting a tumor in the head of a subject to a therapy dose of x-rays comprising moving an orthovoltage range x-ray source on a computed tomography scanning unit including a source, detector, and data processing means for displaying a cross-sectional image of a selected portion of the subject in an arc about the subject such that an x-ray beam from the source is isocentered on the tumor, and directing the beam as a pencil beam to the isocenter in the subject, wherein the beam is collimated to a pencil therapy beam, and including having the beam simultaneously provide a diagnostic image about the isocenter.

* * * * *